(12) United States Patent
Lacoste

(10) Patent No.: US 8,517,943 B2
(45) Date of Patent: Aug. 27, 2013

(54) HEAD FOR IMAGING AND TREATING ORGANS OF LIVING BEINGS AND METHOD FOR MAKING SAME

(75) Inventor: François Lacoste, Paris (FR)

(73) Assignee: Theraclion, Malakoff (FR)

( * ) Notice: Subject to any disclaimer, the term of this patent is extended or adjusted under 35 U.S.C. 154(b) by 740 days.

(21) Appl. No.: 11/921,375

(22) PCT Filed: Jun. 2, 2006

(86) PCT No.: PCT/FR2006/050512
§ 371 (c)(1),
(2), (4) Date: Mar. 11, 2009

(87) PCT Pub. No.: WO2006/129045
PCT Pub. Date: Dec. 7, 2006

(65) Prior Publication Data
US 2009/0216121 A1    Aug. 27, 2009

(30) Foreign Application Priority Data
Jun. 3, 2005    (FR) ...................... 05 51503

(51) Int. Cl.
*A61B 8/00* (2006.01)
(52) U.S. Cl.
USPC ............................ 600/439; 600/407; 600/437
(58) Field of Classification Search
USPC ...................................................... 600/439
See application file for complete search history.

(56) References Cited

U.S. PATENT DOCUMENTS

| | | | | |
|---|---|---|---|---|
| 4,440,025 A | * | 4/1984 | Hayakawa et al. | 73/642 |
| 4,688,576 A | * | 8/1987 | Meyers | 600/446 |
| 4,868,476 A | * | 9/1989 | Respaut | 318/632 |
| 4,955,365 A | | 9/1990 | Fry et al. | |
| 5,036,855 A | | 8/1991 | Fry et al. | |
| 5,197,019 A | | 3/1993 | Delon-Martin et al. | |
| 5,240,002 A | * | 8/1993 | Brisson et al. | 600/439 |
| 5,273,027 A | | 12/1993 | Sekino et al. | |

(Continued)

FOREIGN PATENT DOCUMENTS

| | | |
|---|---|---|
| DE | 42 05 030 A1 | 9/1992 |
| DE | 38 44 672 C2 | 1/1997 |

(Continued)

OTHER PUBLICATIONS

International Search Report for International Application No. PCT/FR2006/050512, date of completion of report, Dec. 1, 2006.

(Continued)

*Primary Examiner* — Unsu Jung
*Assistant Examiner* — Saurel J Selkin
(74) *Attorney, Agent, or Firm* — Mintz Levin Cohn Ferris Glovsky and Popeo, P.C.

(57) ABSTRACT

An imaging and treatment head for imaging and treating an organ or tissue of a living being, and usable in particular for treating tumors of the prostate or the thyroid. The head includes an ultrasonic probe suitable for emitting waves or radiation so as to provide an imaged representation of an organ or tissue for treatment. The head also includes a treatment mechanism suitable for treating the organ or tissue locally. The treatment mechanism is suitable for emitting waves or radiation so as to treat the organ or the tissue. The head is characterized in that the ultrasonic probe is mounted in a removable manner on an adapter that ensures positioning of the ultrasonic probe relative to the treatment mechanism.

11 Claims, 6 Drawing Sheets

(56) References Cited

U.S. PATENT DOCUMENTS

| | | |
|---|---|---|
| 5,391,140 A | 2/1995 | Schaetzle et al. |
| 5,435,304 A | 7/1995 | Oppelt et al. |
| 5,720,287 A | 2/1998 | Chapelon et al. |
| 6,071,238 A | 6/2000 | Chapelon et al. |
| 6,135,964 A | 10/2000 | Barry et al. |
| 6,221,014 B1 | 4/2001 | Bauer |
| 6,488,639 B1 | 12/2002 | Ribault et al. |
| RE38,030 E | 3/2003 | Chapelon et al. |
| 6,676,601 B1 | 1/2004 | Lacoste et al. |
| 2002/0087080 A1 | 7/2002 | Slayton et al. |
| 2004/0254620 A1* | 12/2004 | Lacoste et al. ............ 607/96 |
| 2010/0094177 A1* | 4/2010 | Lacoste ............ 601/2 |

FOREIGN PATENT DOCUMENTS

| | | |
|---|---|---|
| EP | 0 400 196 | 12/1990 |
| EP | 0 734 742 A2 | 10/1996 |
| FR | 2 708 207 A1 | 7/1993 |
| FR | 2 715 822 | 8/1995 |
| FR | 2 827 149 | 1/2003 |

OTHER PUBLICATIONS

International Preliminary Report ori Patentability in French and English Translation for International Application No. PCT/FR2006/050512.

International Search Report for International Application No. PCT/FR2006/050513, date of Completion, Nov. 13, 2006.

International Preliminary Report for Patentability in French and English Translation for International Application No. PCT/FR2008/050513.

International Preliminary Report for Patentability in French and English Translation for International Application No. PCT/FR2006/050514.

French Search Report for Application No. FR 0551503 dated Oct. 17, 2005.

* cited by examiner

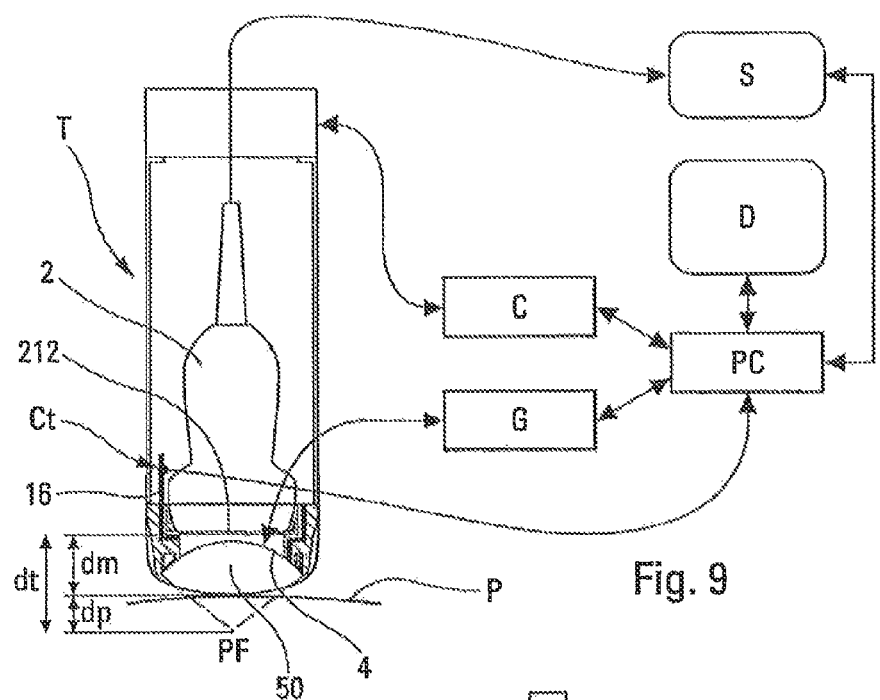
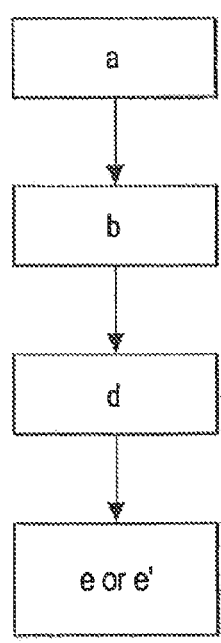
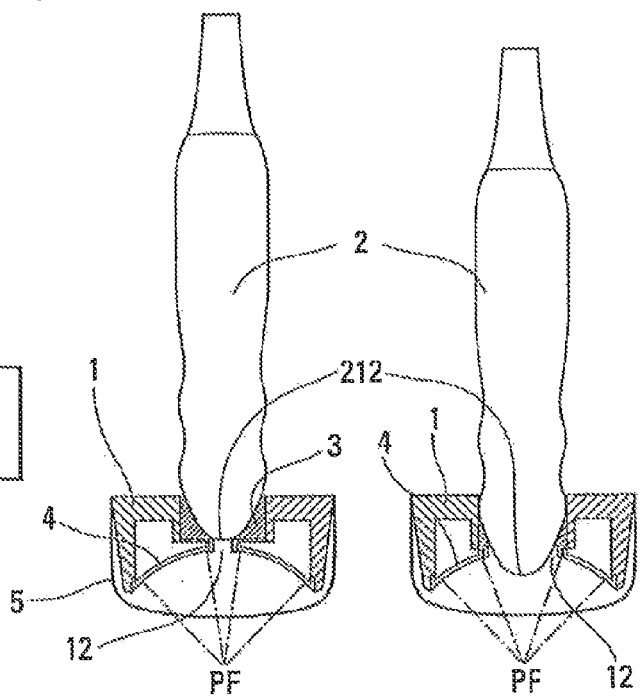
Fig. 9
Fig. 10
Fig. 11a
Fig. 11b

HEAD FOR IMAGING AND TREATING ORGANS OF LIVING BEINGS AND METHOD FOR MAKING SAME

CROSS REFERENCE TO RELATED APPLICATIONS

This application claims priority to PCT application no. PCT/FR2006/050512, having an international filing date of Jun. 2, 2006, and French Patent Application No. 0551503, filed Jun. 3, 2005. Each of the foregoing disclosures is expressly incorporated herein in their entireties.

SUMMARY AND BACKGROUND

The present invention relates to an imaging and treatment head for imaging and treating organs or tissues of living beings, and usable in particular for treating various tumors, such as tumors of the thyroid, breast, or uterus. The present invention also relates to a method of manufacturing a component part of the head. The present invention consequently relates to the field of therapy devices, and more particularly to therapy devices for performing therapy with ultrasound monitoring, and more particularly to therapy devices using power ultrasound. Treatment using focused power ultrasound is known under the acronym HIFU (High Intensity Focused Ultrasound).

The treatment and imaging head of the invention is for mounting on an arm provided with motors, so as to be able to displace the head accurately in various directions. The head is also connected to an electronic control and treatment cabinet, and to a scanner, e.g. an ultrasonic scanner. In addition, the head is generally connected to a cooling unit that causes a refrigerated propagation medium to circulate inside the head. This is a relatively conventional design for an ultrasonic treatment and imaging head using HIFU treatment and an ultrasonic imaging probe, for example. This is only one particular type of treatment device: naturally, other types of treatment device exist that use other imaging and treatment techniques, but without going beyond the ambit of the invention.

The treatment performed by the treatment means of the head may use optionally-focused ultrasound. Amongst treatments using focused ultrasound, treatment using HIFU is already known. The invention preferably, but not exclusively, uses that type of HIFU treatment. Other types of treatment can be used in the ambit of the present invention, and in particular any treatment using waves or radiation that is likely to reach a target that is situated in an organ or a tissue of a living being. The treatment of the present invention is preferably non-invasive: however, invasive treatment can also be envisaged in the ambit of the present invention.

In addition to its treatment means, the imaging and treatment head also includes imaging means that may be of any kind, such as imaging using an ultrasonic probe, an X-ray probe, or IRM, for example. However, imaging using ultrasound is preferred in the ambit of the present invention.

There already exist such imaging and treatment heads that make it possible, in a single unit, to combine the treatment means and the imaging means necessary for locating and showing the target for treatment. It is essential to locate the target for treatment properly, so as to avoid damaging healthy portions of the tissue or of the organ for treatment. To do this, the imaging means must deliver a reliable and accurate representation of the site of the target.

To enable the target for treatment to be located accurately, it is essential for the treatment means and the imaging means to be mutually positioned relative to each other in completely accurate manner. Initially, it is possible to put the imaging means into place, so that they can take an accurate image of the site for treatment. The imaging means may then be moved away and the treatment means are then put into place and positioned very accurately in order to correspond with the image taken by the imaging means. Another technique is to couple the imaging means and the treatment means mechanically on a single head at precise locations.

The imaging means, e.g. an ultrasonic probe, are mounted on the head in an appropriate housing or fastened into place by adhesive. The imaging means are thus integrated in the head. With such a head, the type of imaging means is determined by the head, given that the imaging means are bonded to the head or are installed in a housing specifically for said means. It is therefore not possible to use other imaging means that would perhaps be more appropriate for some particular use or for some particular site for treatment. For example, depending on the organs for treatment, it can be preferable to use ultrasonic probe having a linear or a curved array, or operating in a determined range of frequencies.

An object of the present invention is to overcome the above-mentioned prior-art drawbacks by defining an imaging and treatment head that can be more modular, but without neglecting the accurate positioning of the imaging means relative to the treatment means.

To achieve this object, the present invention proposes that the imaging means are mounted in removable manner on an adapter that ensures positioning of the imaging means relative to the treatment means. Advantageously, the head includes a mounting body including a fastener zone for fastening the treatment means, and a mounting housing for mounting the imaging means, said mounting housing receiving said adapter in which the imaging means are mounted in removable manner. It is therefore the adapter that makes it possible to position the imaging means accurately relative to the mounting body of the head. The adapter thus constitutes an intermediate or transition part that takes into account firstly the shape of the mounting housing of the body, and secondly the shape of the imaging means. The adapter thus makes it possible to couple the imaging means accurately to the head, on which the treatment means are also mounted. However, the adapter enables the imaging means to be independent of the head with regard to the respective shapes of the imaging means and of the mounting housing, since it is the adapter that enables them to be connected together. In this sense, the adapter makes it possible to uncouple the imaging means from the head. Consequently, by using another type of adapter that matches another type of imaging means, it is possible to mount said other imaging means on the head of the invention in accurate and removable manner. Consequently, by providing a set of adapters that are compatible with a wide range of imaging means, it is possible to mount any imaging means on the head of the invention.

In an advantageous embodiment, the head includes a propagation space containing a propagation medium that is suitable for transmitting the waves or radiation emitted by the imaging means and/or the treatment means, the body forming a window that puts the housing into communication with the propagation space, said imaging means including a tip portion and a base portion, said tip portion incorporating an emitter/receiver face for emitting/receiving waves or radiation, and for being received in the adapter in such a manner as to emit through the window in the propagation space. The adapter preferably includes a front wall that is positioned in front of the emitter face of the imaging means and that closes the window at least in part, said front wall forming a diverging lens that is suitable for distancing the focal point of the waves or radiation emitted through the lens and the propagation space. The adapter is thus used to displace the focal point of the imaging means. This is particularly advantageous when an ultrasonic probe is used having a wave emitter/receiver face that is normally for coming into direct contact with the skin of the patient. However, in an imaging and treatment head, the emitter/receiver face of the ultrasonic probe is not in contact with the skin of the patent, but is offset by a distance of about 3 centimeters (cm). This is why it is necessary to distance the focal point of the waves emitted by the ultrasonic probe by a distance of about 3 cm. In the present invention, the adapter is used to form the diverging lens that makes it possible to offset the focal point of the ultrasonic probe by a distance of about a few centimeters, preferably 3 cm. Between the emitter/receiver face of the probe and the skin of the patient, the waves propagate through the propagation space that is filled with a propagation medium that is conventionally water.

According to another advantageous characteristic of the invention, the adapter includes a sealing ring that ensures sealing between the imaging means and the mounting housing, the imaging means advantageously deforming the ring while they are being inserted into the ring. Thus, in addition to its function of positioning the treatment means, the adapter also provides a sealing function that is advantageously improved by the ring deforming in such a manner as to create intimate contact between the ring and the mounting housing and between the ring and the imaging means. The adapter thus performs a role of a sealing gasket. The adapter is advantageously made of elastomer material.

The sealing ring may be combined with the optionally-diverging lens. The emitter/receiver face of the imaging means is then in direct contact with the propagation medium of the propagation space.

According to another characteristic of the invention, the imaging means are held in position in said adapter by means of a holding system that is suitable for urging the imaging means into said adapter. The holding system thus presses the imaging means against the adapter that is thus wedged between the imaging means and the mounting housing of the body. The holding system thus makes it possible to block the imaging means in the adapter, thereby providing accurate positioning of the emitter/receiver face of the imaging means relative to the treatment means. In addition, the thrust force created by the holding system improves the sealing at the adapter.

In an advantageous embodiment, the imaging means comprise an ultrasonic probe having a linear array. The body preferably forms an elongate window, the linear array being positioned so as to emit through the window, the treatment means being positioned on either side of the elongate window. The use of a linear-array ultrasonic probe disposed in a midplane, dividing the treatment means into two substantially identical portions, is a characteristic that may be protected independently of the fact that the imaging means are mounted in removable manner on an adapter. In other words, this characteristic may be protected independently.

In addition, the treatment means may comprise a focused piezoelectric transducer of the HIFU type. Thus, both the imaging means and the treatment means use ultrasonic, such that the propagation space may be filled with a propagation medium that is appropriate both for the imaging means and for the treatment means.

The invention also provides a method of manufacturing an adapter for imaging means incorporated in a focused-imaging/treatment head according to any preceding claim, in which said method comprises the steps of:

a) providing imaging means that include a tip portion that includes an emitter face through which waves or radiation are transmitted;

b) digitally scanning said tip portion of the imaging means in order to obtain a geometrical representation and an accurate estimation of the dimensions of said tip portion;

c) providing a mold that presents a shape and dimensions that match the result obtained in step b); and d) pouring one or more elastomeric materials into the mold so as to obtain a molded product that forms an adapter that is suitable for being positioned accurately on the tip portion of the imaging means.

Advantageously, the mold is made with dimensions that are slightly smaller than the tip portion, such that the adapter is naturally compressed while the imaging means are inserted in the head.

BRIEF DESCRIPTON OF THE FIGURES

The invention is described more fully below with reference to the accompanying drawings which show several embodiments of the invention as non-limiting examples.

FIG. 9 is an overall diagrammatic view of a complete treatment appliance that is suitable for incorporating the imaging and treatment head of the invention;

FIG. 10 is a flow chart showing the various steps of the method of determining the real distance to the target; and FIGS. 11a and 11b are diagrammatic views in vertical section of two head configurations that differ in the positioning of the imaging probe.

DETAILED DESCRIPTION

Figure 1:
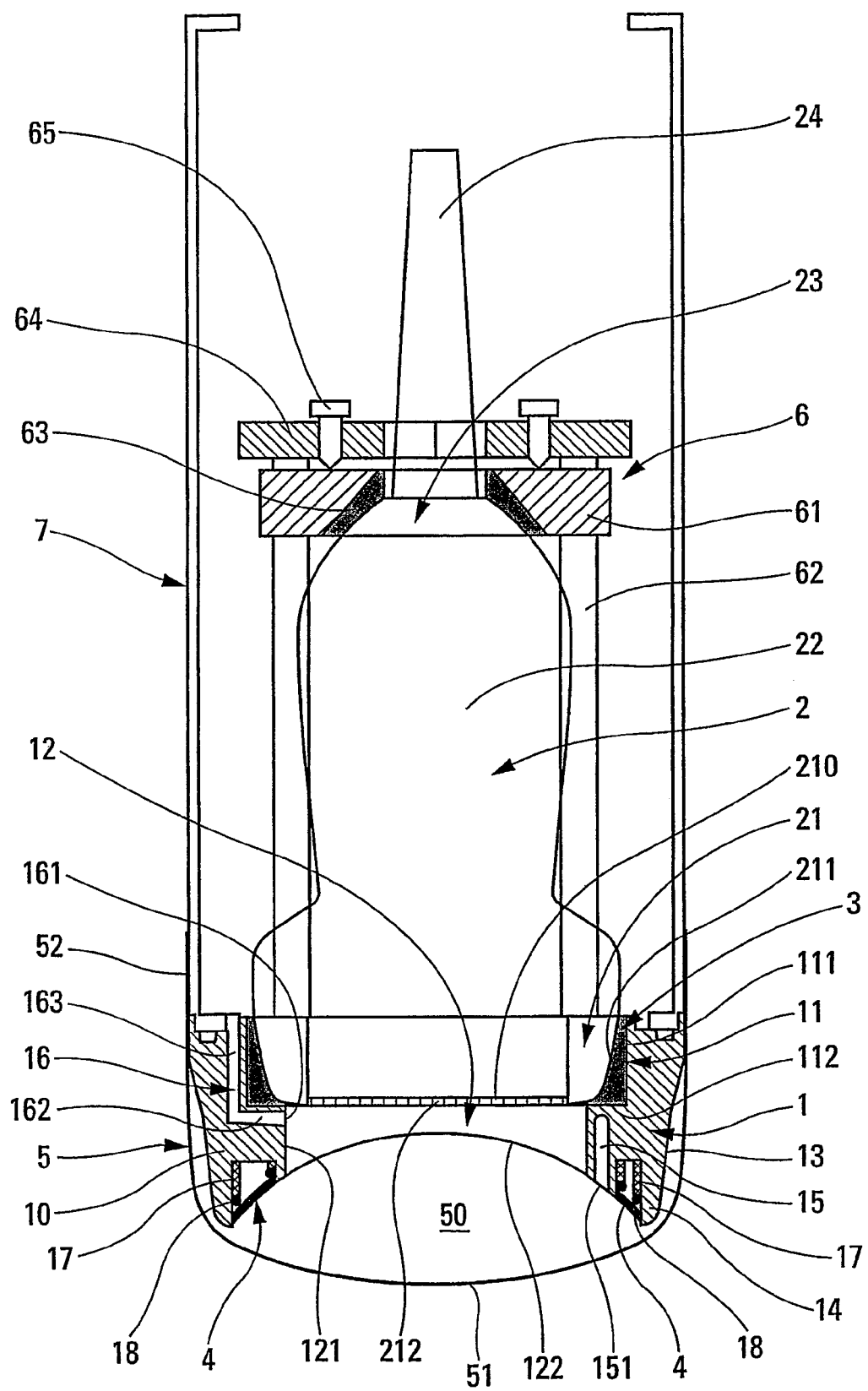
FIG. 1 is a vertical section view through a treatment and imaging head constituting a first embodiment of the invention.
Figure 2:
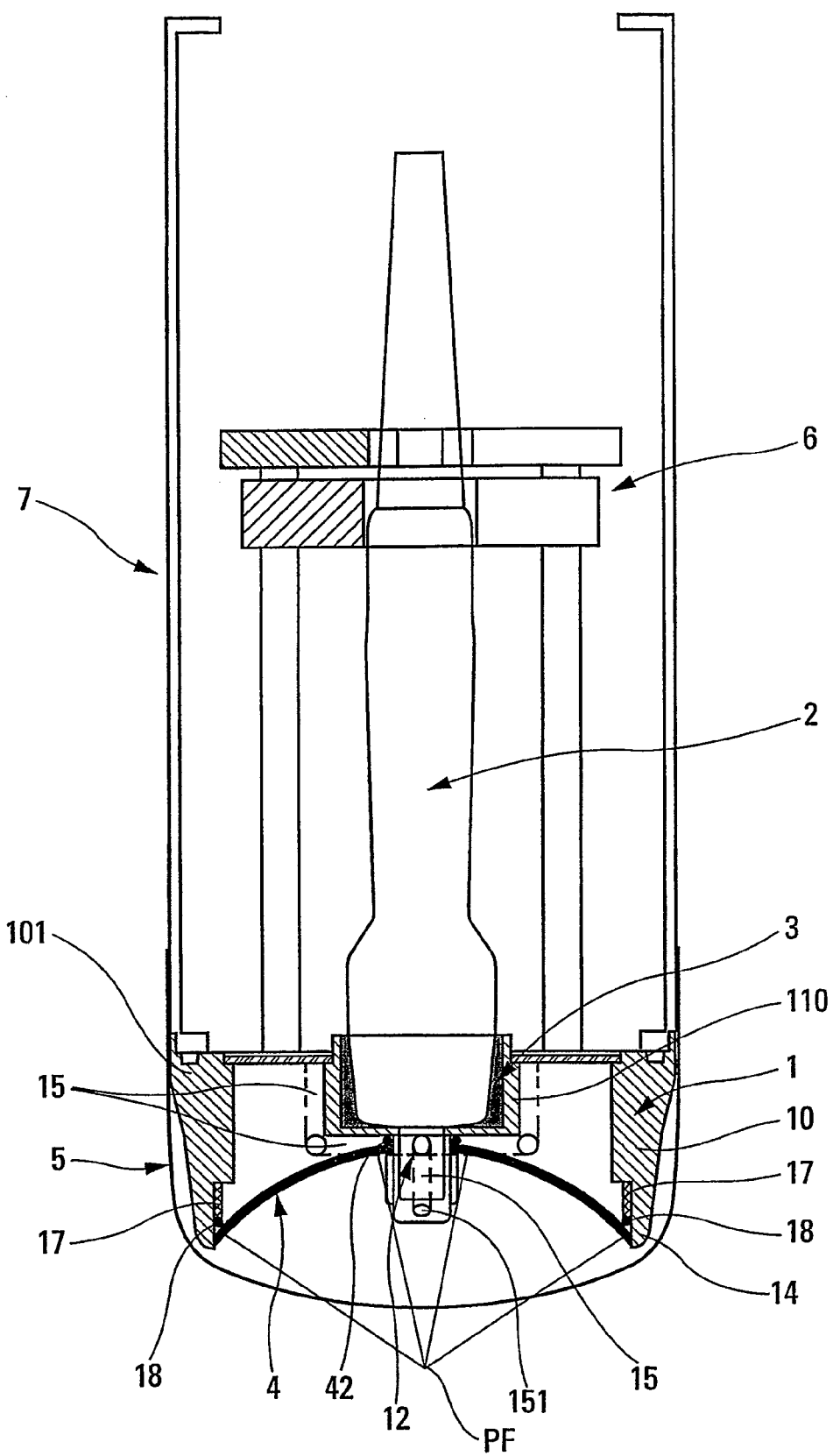
FIG. 2 is a view similar to the view in FIG. 1 along a vertical section plane that is offset by 90° relative to the plane in FIG. 1.
Figure 3:
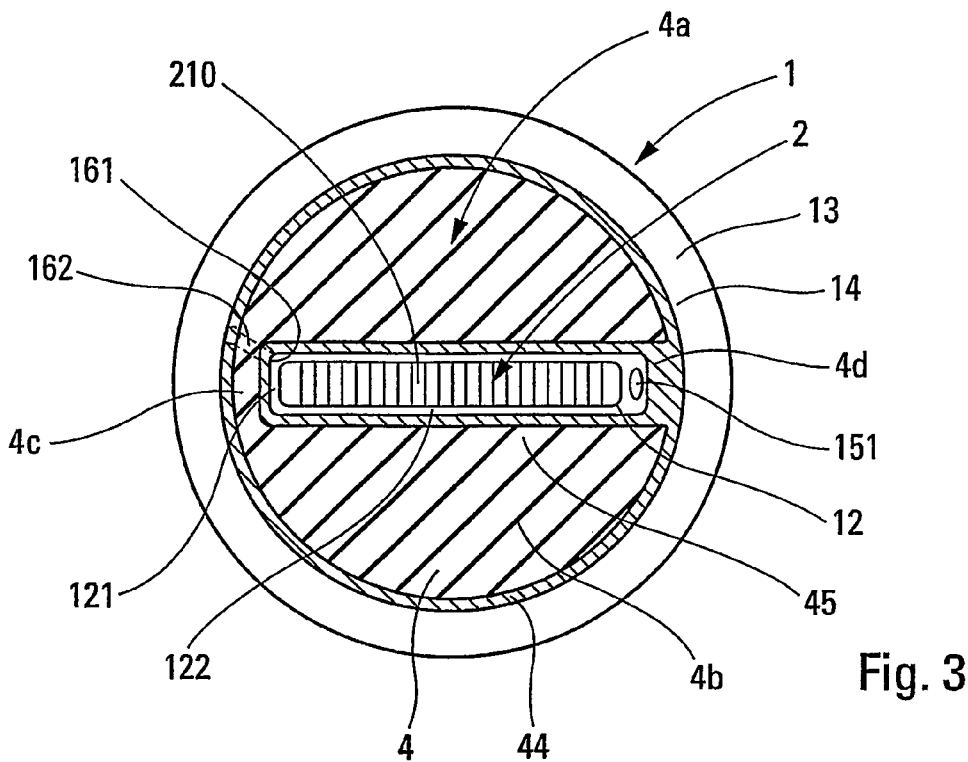
FIG. 3 is a view from below of the head in FIGS. 1 and 2, with the balloon removed.

Reference is made firstly to FIGS. 1, 2, and 3 for explaining in detail the structure and the operation of an imaging and treatment head constituting the first embodiment of the invention. The same general structure is also used in the third and fourth embodiments of FIGS. 6, 7, and 8, whereas the embodiments of FIGS. 4 and 5 do not incorporate imaging means, merely treatment means.

The head of FIGS. 1 to 3 comprises seven component elements, namely a mounting body 1, imaging means 2, an adapter 3, treatment means 4, a balloon 5, a holding system 6, and a casing 7.

In this embodiment, the imaging means 2 are constituted by an ultrasonic imaging probe, and the term "probe" is used to designate the imaging means in the remainder of the description. However, it should be understood that such a probe is not the only device that can be used as imaging means. It is also possible to use X-ray probes or IRM probes, this list not being exhaustive. Any imaging means can be used.

In this embodiment, the treatment means 4 are constituted by a therapy device that can use optionally-focused ultrasound. The technique using focused ultrasound is conventionally designated by the abbreviation "HIFU". In the description below, the treatment means are designated by the term "HIFU transducer". However, it should be understood that the HIFU transducer is not the only device that can be used as treatment means. It is possible to use any invasive, or preferably non-invasive, device that is capable of reaching a target that is situated in an organ or tissue of a living being.

The mounting body 1 is a part, preferably made as a single piece, that is made of any appropriate material such as plastics material, metal, ceramic, or composite. The body 1 is preferably made by machining or molding metal, e.g. aluminum or stainless steel. The mounting body 1 constitutes a kind of central carrier part for carrying the imaging and treatment head constituting this embodiment of the invention. The mounting body 1 serves to mount the ultrasonic probe 2, the HIFU transducer 4, and the balloon 5. The body 1 is mounted on the casing 7 that serves to fasten the head on a hinged arm (not shown). The holding system 6 is also mounted on the body 1 for holding the ultrasonic probe 2 axially in place on the body 1.

The body 1 presents a general configuration that is generally circularly cylindrical. The body 1 includes a crown 10 of generally cylindrical shape, with an outer wall 13 that is substantially frustoconical or flared. The crown 10 includes an anchor heel 101 for fastening the body 1 onto the casing 7. The body 1 also includes an annular free end-edge 14 at its end remote from the anchor heel 101. Inside the crown 10, the body 1 forms a mounting housing 11 for receiving the ultrasonic probe 2, as described below. The housing 11 presents an elongate shape that extends across the crown 10 diametrally. The crown 10 forms the two ends of the housing 11 that are interconnected via two longitudinal walls 110 that extend across the crown. The housing 11 presents a configuration that is substantially a rectangular parallelepiped, as can be understood from FIGS. 1, 2, and 3. The housing 11 includes an inner side wall 111 that extends in rectangular manner, and an end wall 112. The wall 111 advantageously flares upwards. The wall 11 is preferably lined with an absorbent material so as to avoid acoustic reflections that would otherwise degrade the image. The wall 112 is formed with an opening that opens to a window 12 that presents a configuration that is substantially similar to the configuration of the housing 11. The window 12 is elongate and extends in diametral manner from one side of the crown to the other, as can be seen in FIG. 1. The window 12 is bordered by side walls 121 that are formed by the crown, and by side walls 122 that extend across the crown, as can be seen in FIG. 3. The elongate housing 11 thus communicates directly with the elongate window 12. More precisely, the end wall 112 of the housing 11 is extended downwards by the side walls 121 and 122 of the window 12.

Beyond the window 12, the body 1 forms a fastener zone for fastening the HIFU transducer.

The fastener zone presents a shape that is very complex. The fastener zone firstly extends over all or some of the inner periphery of the free end-edge 14 of the body 1. The zone also extends all around the window 12, i.e. over the edge of the walls 121 and 122 of the window 12. This is more visible in FIG. 3. As described below, the HIFU transducer 4 extends over all of the area defined by the edge 14, with the exception of the window 12. This is visible in FIG. 3. As can be seen in FIGS. 1 and 2, the edges of the walls 122 are made in concave curved manner, thereby imparting a concave configuration to the head as a whole. The edge 14 is circular but the edges of the walls 122 are concave. The concave side of the head is preferably spherical in shape, with a radius of curvature that is determined so that the rays converge towards a focal point FP that is visible in FIG. 2. In FIG. 1, it can even be observed that the concave shape of the walls 122 is such that the window 12 is reduced to a minimum at its central portion. At this location, the edge of the wall 122 is very close to the housing 11.

In FIG. 2, the window 12 is shown partially in perspective, so as to reveal characteristics that are not situated in the section plane. Such a characteristic relates more particularly to a feed channel for supplying a propagation medium, and that is designated by numerical reference 15. The channel 15 opens out at the concave formation of the body 1 at an inlet 151 that is situated in line with the window 12, as can be understood from FIGS. 1 and 3. The inlet 151 is formed in the crown 14 in the proximity of the fastener zone for the HIFU transducer. The feed channel 15 then extends inside the body 1 going round the mounting housing 11. This is visible in FIG. 2.

In addition, the mounting body 1 also forms an evacuation channel for evacuating propagation medium, said channel being designated by numerical reference 16. The evacuation channel 16 includes an outlet 161 that opens out in the side wall 121 of the window 12, in the direct proximity of the housing 11. In the embodiment in FIGS. 1, 2, and 3, the evacuation channel 16 includes a radial section 162 that extends below the housing 11, and an axial section 163 that extends vertically just beside the housing 11. The section 163 then opens out above the body 1 where it can be connected to an evacuation tube. The same applies for the channel 15 that can likewise be connected to a feed tube. In a variant shown in FIG. 6, the evacuation channel 16' can include a radial section 162' that passes transversally through the crown 10 so as to open out in the outer wall 13. Then, the propagation medium sucked through the radial section 162' can flow through a substantially axial section 163' that opens out in the anchor heel 101.

The ultrasonic probe 2, which in this embodiment acts as imaging means, is an entirely conventional model available on the market. The ultrasonic probe 2 is a probe having a linear array 210. In typical manner, the probe includes a bottom end or tip portion 21, a body 22, and a top end or base portion 23. The base portion 23 is further provided with a connection sleeve 24, so as to connect the probe to power supply means and means for processing the image taken. The linear elements 210 are disposed side by side at the tip portion 21. The linear array defines a wave emitter and receiver face 212 that presents a rectangular, elongate configuration. Around said face 212, the tip portion 21 defines an outer wall 211 having the general shape of a rounded rectangle. Such a shape is typical for an ultrasonic probe: naturally it is possible to imagine ultrasonic probes having other shapes. However, all probes include an emitter face for emitting waves or radiation, a tip portion, and a base portion.

The ultrasonic probe 2 is positioned in accurate, stationary, and stable manner relative to the body 1 by means of the adapter 3. More precisely, the tip portion 22 of the ultrasonic probe 2 is positioned and held inside the housing 11 formed by the body 1 by means of the adapter 3. The adapter 3 is preferably made of an elastically-deformable flexible material such as an elastomer. The adapter 3 makes it possible to couple the ultrasonic probe 2 to the body 1, thereby guaranteeing accurate positioning of the face 212, and possibly sealing at the housing 11. The adapter 3 is inserted into the housing 11, coming into contact both with the side wall 111 and with the end wall 112. The contact between the adapter 3 and the housing 11 is preferably fluidtight. The adapter 3 thus presents an elongate, substantially rectangular outside shape that corresponds to the shape of the housing 11. Internally, the adapter 3 forms an inner wall that matches the shape of the peripheral outer wall 211 of the tip portion 21. Intimate leaktight contact is preferably created between the wall 211 and the adapter 3. In summary, the adapter 3 presents an outside shape that matches the housing 11, and an inside shape that matches the tip portion of the ultrasonic probe. The adapter 3 defines an elongate passage that corresponds approximately to the opening that puts the housing 11 into communication with the window 12. It is also possible to say that the passage formed by the adapter 3 enables the emitter face 212 of the ultrasonic probe to emit through the window 12. Another definition would be that the emitter face 212 closes the window 12 at the housing 11. Thus, in this embodiment, the adapter 3 is in the form of a positioning and sealing ring having the shape of a generally rectangular torus with a central passage for receiving the tip portion 21 of the ultrasonic probe 2 in such a manner that the emitter face can emit through the window 12. In this embodiment, the adapter surrounds or encircles the tip portion 21, leaving the emitter/receiver face 212 uncovered, so that it can emit directly without having to pass through the adapter.

The adapter 3 can be manufactured using any manufacturing method or technique. For example, it is possible to make the adapter as follows. Firstly, a digitally-scanned impression is taken of the tip portion of the ultrasonic probe 2 in order to obtain a geometrical representation and an accurate estimation of the dimensions of said tip portion. Then a mold part is made using the dimensions taken while scanning the tip portion of the probe. The mold part defines the inside profile of the adapter that is to receive the tip portion of the probe. The mold dimension is preferably slightly smaller, such that the adapter is slightly smaller than the tip portion of the probe. Thus, the tip portion of the probe is force fitted into the adapter, deforming it slightly. The not only provides stable positioning of the probe in the adapter, but also provides perfect sealing. With regard to the outer portion of the adapter, it is made with another mold part that corresponds exactly or approximately to the dimensions of the housing 11 of the body 1. Thus, the adapter is made by means of two mold parts, with one part corresponding to the shape of the probe 2, and the other part corresponding to the shape of the housing 11.

The adapter 3 makes it possible to position the tip portion 21 of the probe 2 in accurate, stable, and leaktight manner on the body 1. In order to hold the probe 2 in completely axial manner, a holding system 6 is also provided that comes into engagement with the base portion 23 of the probe. The holding system 6 thus performs a function of holding the probe axially in the adapter 3, and a function of thrusting or urging the probe into said adapter 3. In this non-limiting embodiment, the holding system 6 comprises a U-clamp formed by longitudinal slide rods 62 and by a stationary plate 64 provided with thrust screws 65. The slide rods 62 are connected to the body 1 using any appropriate means. A thrust plate 61 is slidably mounted on the rods 62 and can be urged to move by the screws 65. The plate 61 is advantageously provided with a thrust ring 63 that comes into contact with the base portion 23 of the probe. The thrust ring 63 can be made in the same way as the adapter 3. The outer portion of the thrust ring 63 matches the substantially frustoconical shape of the thrust plate. In symmetrical manner, the inside face of the thrust ring 63 matches the particular shape of the base portion 23. The base portion 23 is thus positioned in accurate and stable manner in the thrust plate 61. By acting on the thrust screws 65, the thrust plate 61 can be displaced towards the body 1, thereby thrusting the tip portion 21 into the adapter 3 with a controlled force. The thrust ring 63 performs a role that is completely symmetrical to the role of the adapter 3 at the thrust plate 61.

The HIFU transducer 4 is fastened on the mounting body 1 where it forms the concave configuration that is preferably spherical. The transducer 4 also presents a concave shape that is preferably spherical. As can be seen in FIG. 3, the transducer 4 extends inside the edge 14 over the entire area, except at the window 12. In the embodiment in FIG. 3, the transducer 4 can thus be divided into four distinct zones, namely a zone 4a that is situated above the window 12, a zone 4b that is situated below the window 12, a zone 4c that is situated to the left of the window 12, and a zone 4d that is situated to the right of the window 12. It should thus be observed that the transducer 4 completely surrounds the window 12. It should also be observed that the window 12 intersects the transducer 4 substantially in a mid-plane, thereby defining the two large zones 4a and 4b that are of substantially identical size, and are also of symmetrically identical shape about the window 12. The symmetry is mirror symmetry. The zones 4c and 4d constitute junction zones on either side of the window, which junction zones connect the zone 4a to the zone 4b. It should also be observed that the transducer 4 does not extend over the inlet 151 of the feed channel 15 for supplying propagation medium. In FIG. 3, it can be seen that the transducer 4 includes a peripheral-edge zone 44, and a window-edge zone 45. They are shown darker than the remainder of the transducer 4 that is hatched. The edges 44, 45 and the zone 4d constitute the locations via which the transducer 4 is fastened on the fastener zone of the body. In the variant embodiment shown in FIG. 8, the transducer 4 includes only two zones 4a and 4b that are separate from each other. There are no zones 4c and 4d in this embodiment. Instead, the body forms two areas 141 that connect the edge 14 to the window 12. The inlet 151 is formed in one of the two areas 141. The transducer 4 thus extends over a fraction only of the edge or of the periphery.

Figure 4:
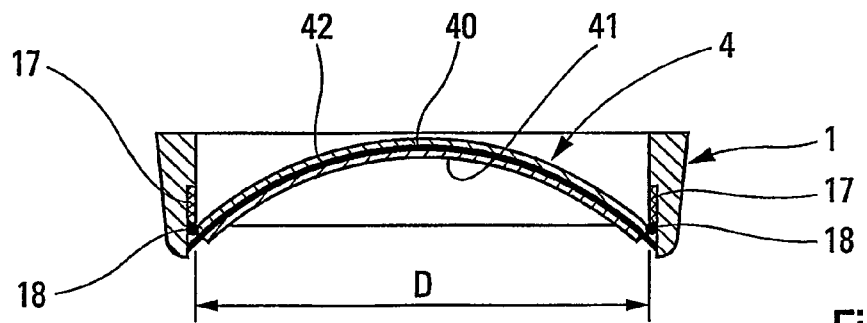
FIG. 4 is a fragmentary section view of a treatment head constituting a second embodiment of the invention.
Figure 5:
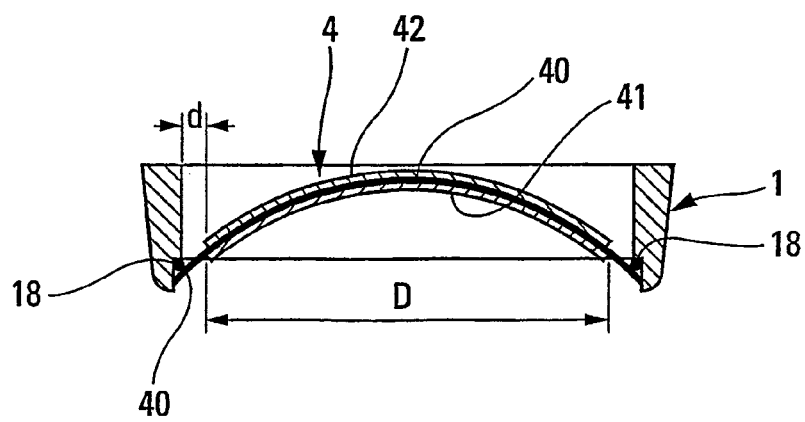
FIG. 5 is a view similar to the view in FIG. 4 for a prior-art treatment head.

Reference is made below to FIGS. 4 and 5 in order to explain how the active working surface area of the transducer 4 is extended in the invention compared to prior-art transducers. FIG. 5 shows a prior-art transducer mounted on a mounting body of a conventional treatment head that does not incorporate imaging means. This is why the transducer 4 is not interrupted by the window 12, as occurs with the imaging and treatment head of FIGS. 1 to 3. In this prior-art embodiment, the transducer 4 comprises, in conventional manner, a piezoelectric element 40 that can be made from one or more piezoelectric parts. The piezoelectric element 40 presents a concave shape that is preferably spherical. The element 40 can be completely circular or it can present some other shape. In order to cause the piezoelectric element 40 to vibrate, an active electrode 42 is provided that extends over the convex face of the element 40. On its concave face, the element 40 is provided with a ground electrode 41. The electrodes 41 and 42 extend over a major fraction of the surface area of the piezoelectric element 40, in such a manner as to be suitable for exciting it in maximum manner. The piezoelectric element 40 is fastened to the body 1 at a fastener zone by means of an adhesive joint 18. The adhesive joint 18 can advantageously be housed in a recess formed by the body 1. Given that the body 1 is generally made of metal, such as aluminum or stainless steel, it is not possible to extend the active electrode 42 until it comes into contact with the body 1. It is not even possible for it to come close to the body 1, without risk of creating electric arcs. Consequently, it is necessary to stop the active electrode 42 at some minimum distance d from the body 1, as can be seen in FIG. 5. Consequently, an edge zone of the piezoelectric element 40 is not excited, thereby reducing the active working surface area of the transducer 4 considerably.

FIG. 4 shows how the present invention solves the problem of reducing the active surface area of the transducer 4. In the invention, an electrically-insulating trim 17 is applied on the body 1 where the active electrode 42 is close to the body 1. It is also possible to apply an insulating trim on the transducer instead of, or as a complement to, the insulating trim of the body. The adhesive joint 18 that makes it possible to fasten the transducer 4 to the body 1 can be applied on the body 1, or advantageously on the electrically-insulating trim 17. The active electrode 42 can thus extend as far as the adhesive joint 18, without risk of creating electric arcs, as a result of the presence of the trim 17. The trim 17 extends over the body 1 wherever the transducer 4 is fastened to the body 1. Such a sealing trim 17 can be used on any treatment head optionally using imaging means. In FIG. 4, the treatment head, shown in part, does not incorporate imaging means. In contrast, in the embodiment in FIGS. 1 to 3, the head incorporates imaging means, and the transducer 4 is fastened to the body 1 by means of adhesive joints 18 that are associated with pieces of sealing trim 17, visible in FIGS. 1 and 2. The electrically-insulating trims 17 can be made of any appropriate material, such as plastics material, for example. It is even possible to envisage using the sealing trim 17 to fasten the transducer 4 on the body 1. In this event, the trim is in the form of a substantially-rigid part that is dimensioned with precision and positioned on the mounting body. The transducer is mounted directly on the trim that thus serves as support means. If necessary, the adhesive can be applied on the trim. The trim can have the shape of a rigid insulating ring that matches both the shape of the body and of the transducer. The trim can be mounted by being overmolded on the body. By means of the insulating trim 17, the active working surface area of the transducer 4 can be increased by about 20% compared to a prior-art transducer, such as the transducer shown in FIG. 5. Using the insulating trim 17 is more particularly recommended at the edge 14, given that the increase in active surface area is greater at that point, whereas it is smaller at the window 12, because of its central position.

To complete the imaging and treatment head of the embodiment in FIGS. 1 and 2, the balloon 5 that is made of a material that is flexible and preferably elastically deformable, comes to cover the head 1. The balloon 5 is fastened in leaktight manner on the body 1 at its anchor heel 101. The transducer 4 and the window 12 in which the array 210 is situated are thus covered by the balloon 5. Given that the transducer 4 is fastened in leaktight manner to the body 1, and that the array 210 is fastened in leaktight manner in the housing 110, there is created with the balloon 5 an internal propagation space 50 that can advantageously be filled with a propagation medium for propagating the waves emitted by the probe 2 and the transducer 4. In practice, the propagation medium can be water or ultrasonic gel. The propagation space 50 extends in the concave shape of the transducer 4, and extends as far as the outer wall 13 of the body 1. Given that the HIFU transducer 4 generates heat that is focused at the focal point FP (FIG. 2), the waves pass through the propagation medium situated in the space 50. The heat produced by the transducer 4 thus heats up the propagation medium. In order to avoid an excessive increase in the temperature of the propagation medium, it is known to cause the propagation medium to circulate inside the propagation space 50. To do this, the head is fed with water, and has water evacuated therefrom. More precisely, and as mentioned above, the body 1 forms a feed channel 15 and an evacuation channel 16 or 16'. The water penetrates into the space 50 via the feed channel 15, and leaves said space via the evacuation channel 16 or 16'. A constant and relatively low temperature is thus guaranteed for the propagation medium. Furthermore, in order to avoid the formation of bubbles inside the propagation space, the invention situates the outlet 161 to the evacuation channel 16 or 16' at the window 12, and preferably as close as possible to the emitter face 212 of the probe. It has been found in empirical manner that the bubbles tend to accumulate at the emitter face of the probe, thereby creating a veil through which the probe cannot emit without unwanted diffractions. By positioning the outlet 161 as high as possible in the proximity of the emitter face, the formation of such a veil of bubbles is avoided.

Figure 6:
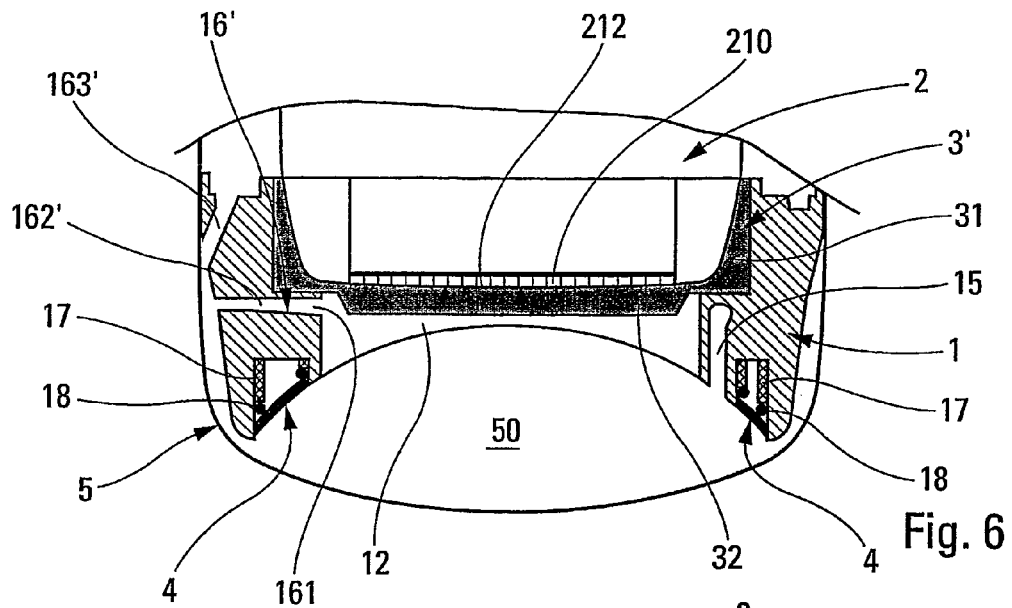
FIG. 6 is a fragmentary view similar to the view in FIG. 1 constituting a third embodiment of the invention.
Figure 7:
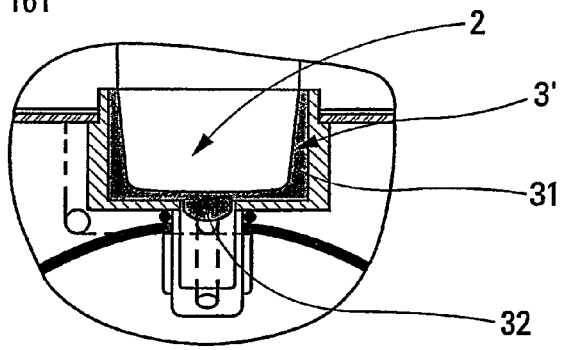
FIG. 7 is a fragmentary view, similar to the view in FIG. 2, of the FIG. 6 head.
Figure 8:
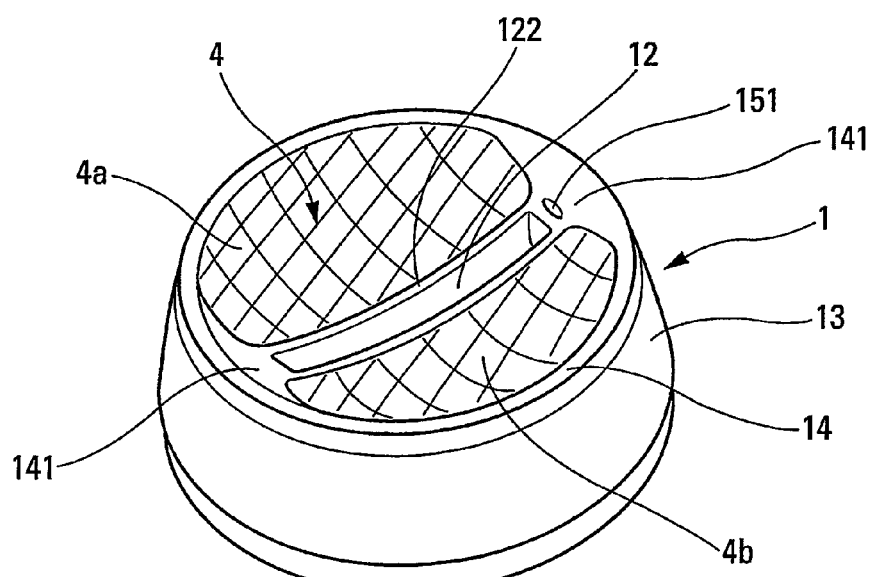
FIG. 8 is a diagrammatic perspective view of a treatment and imaging head constituting a fourth embodiment of the invention.

Reference is made below to FIGS. 6 and 7 in order to explain an advantageous variant embodiment of the adapter. While the adapter 3 in FIGS. 1 and 2 forms only a sealing and positioning ring engaged around the probe, leaving the emitter face uncovered, the adapter 3' in FIGS. 6 and 7 includes a front wall 32 that extends in front of the emitter face of the probe and that simultaneously closes the opening between the housing 11 and the window 12. The emitter face of the probe is thus no longer in contact with the propagation medium present in the propagation space 50. The adapter 3' thus forms a kind of sheath that surrounds the entire bottom portion of the probe. The front wall 32 is advantageously made such that it forms a diverging lens that is disposed in front of the emitter face of the probe so as to distance or displace the focal point of the waves emitted by the probe by a distance of a few centimeters, advantageously 2 cm. While the focal point of the ultrasonic probe would normally be situated at the balloon 5, the diverging lens 32 makes it possible to displace the focal point outwards from the balloon by a distance of a few centimeters, so as to be able to provide a reliable representation of an organ or tissue of a living being that is situated two centimeters below the skin. Consequently, the adapter 3' must be made of an appropriate material that allows ultrasound generated by the probe to pass therethrough.

Another advantageous characteristic of the invention resides in the fact that the probe extends substantially in a mid-plane relative to the transducer, thereby dividing it into two substantially identical portions by mirror symmetry. More precisely, the window 12 that receives the face 212 subdivides the transducer into two. It is particularly advantageous to use a probe having a plane or linear array with this configuration. It is also easy to vary the position of the face 212 relative to the transducer by widening or narrowing the width of the window 12, as can be understood from FIGS. 11a and 11b.

The above-described head(s) can be incorporated in a treatment appliance as shown diagrammatically in FIG. 9. In this appliance, the head T is associated with a plurality of elements such as, for example, a power generator G for powering the treatment means (transducer 4), a displacement controller C for displacing the head, an ultrasound scanner S connected to the probe 2, a display screen D, and a computer PC that serves to manage the appliance. All of the elements of the appliance are connected to the PC. The screen D serves to display the target site sensed by the probe of the head connected to the scanner S. Furthermore, the evacuation channel 16 of the head is provided with a temperature sensor Ct that is suitable for measuring the temperature of the propagation medium that leaves the propagation space. The measurement is sent directly to the PC. The use of the temperature measurement is explained below. The emitter/receiver face of the head emits waves that pass firstly through the propagation medium over a certain thickness dm, and then through the living tissue over another thickness dp, i.e. over a total thickness dt.

In this respect, there exists a problem of determining the distance between the emitter/receiver face of the probe and the target site to be displayed and then treated. The ultrasonic probe is remote from the patient, and ultrasound emitted and received by the ultrasonic probe propagates through the refrigerated propagation liquid over a significant distance. However, it is known that the speed of ultrasound depends on the temperature of the medium and on the nature of medium. In contrast, ultrasonographs are adjusted on the principle that ultrasound propagates through the tissue of the patient, and thus calculates the distance to the target from the speed in a typical tissue that is assumed to be at 37° C. However, for an imaging head that also incorporates treatment means, the waves emitted by the probe must pass through a certain thickness of propagation medium that is advantageously maintained at a constant temperature of the order of about 10° C. Consequently, not only must the waves travel over a distance that is greater than the distance traveled when a probe is applied directly to the skin of the patient, but it must also pass through a medium that is different from living tissue both in nature and in temperature. Passing through the propagation medium thus induces an aberration in calculating the distance to the target that it is appropriate to correct in order to be able to perform treatment that is accurate and effective.

Sound propagates more slowly in the propagation medium than in the tissue. The ultrasonograph interprets this increased travel time as a greater distance, and the target thus appears further than it really is. The example given shows that the offset can be significant, in particular for highly focused systems in which the position of the focal point is very accurate.

Unfortunately, the concentration point of therapeutic ultrasound emitted by the treatment means is generally modified little or not at all by the temperature of the medium. Ultrasound emitted by the treatment means e.g. a transducer 4, always concentrates at the center of the sphere. In a different system, the effect of the ultrasound can be modified by temperature, and it is thus prudent to take temperature into account.

The flow chart shown in FIG. 10 is a diagram showing the various steps of the method of determining the real distance between the face 212 and the target. Starting at a), the temperature of the propagation medium is measured by means of the sensor Ct. Then at b), the propagation speed of the waves from the probe in the propagation medium at the temperature measured at a) is calculated. At c), the thickness of the propagation medium through which the waves pass is determined or known. At d), it is thus possible to calculate the distance error or correction.

Assuming, for example, that:
the target is located at the focal point of the transducer 4, at 40 millimeters (mm) from the emitter/receiver face of the probe;
the target is located at dp=15 mm below the skin. The waves must therefore pass through a thickness dm=25 mm of propagation medium; and
the propagation medium is water that is refrigerated to 10° C., having a speed that is 1449 meters per second (m/s). The speed can be determined from tables of values that have been pre-established as a function of the nature of the propagation medium, typically water.

The distance correction can thus be determined by means of software loaded in the PC. The correction is equal to 1.2 mm.

It is possible to attribute the distance correction in several ways, as indicated in FIG. 10. For example, in the appliance in FIG. 9, the ultrasonic image coming from the probe is reproduced on the screen D of the computer PC, on which the position of the focal point is also shown by a mark. A first correction can consist in modifying the position of the focal point mark by the calculated distance. In the present example, the probe provides the position of the target as being at 41.2 mm from the face 212, and it is therefore necessary to move the mark closer to the focal point through 1.2 mm towards the origin of the ultrasonic image. A second correction can consist merely in displacing the treatment head along its axis when in operation, (in the present example moving it back through 1.2 mm). Both possibilities of applying the distance correction are represented by e and e' in FIG. 10. A third correction can consist in modifying the parameters of the ultrasonograph, e.g. its internal value for the speed of sound in the tissues.

Figure 12:
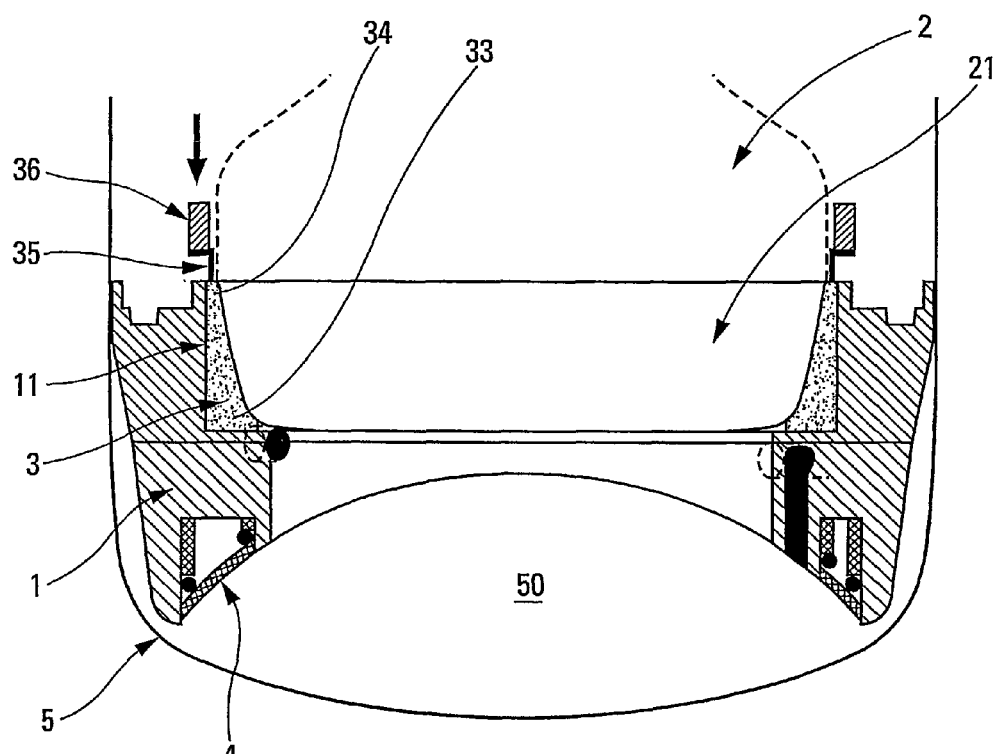
FIGS. 12, 13a and 13b illustrate exemplary adapter, according to some embodiments of the current subject matter.
Figure 13A:
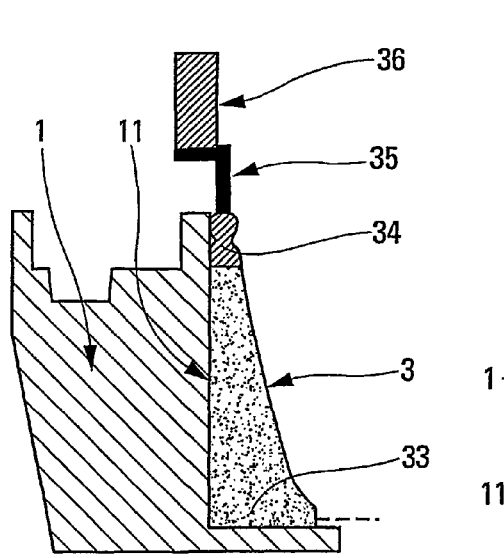
Figure 13B:
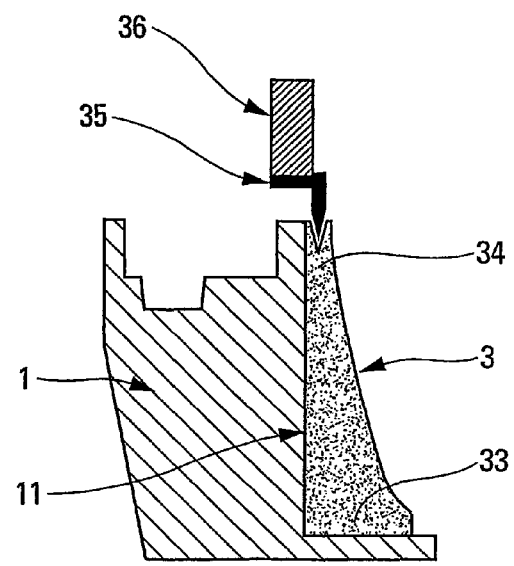

With reference below to FIGS. 12, 13a, and 13b, it can be seen that the adapter 3 can be compressed, deformed, or expanded sideways in its housing 11 by a compression bushing 35 that is itself urged by a thrust part 36 that exerts a force on the bushing in the direction of the arrow shown in FIG. 12. The adapter 3 includes a bottom portion 33 that is thicker, and as a result is more rigid and more stable in size. On its opposite side, the adapter includes a top portion 34 that is thinner, and as a result is deformable. The bushing bears against the adapter at the deformable top portion. Thus, the top portion deforms by flattening axially and by expanding sideways in such a manner as to advantageously bear in leaktight manner against the tip portion 21 of the probe 2. The rigid bottom portion remains substantially undeformed and thus provides accurate and stable positioning of the probe. The bushing bears against the adapter around the entire probe, preferably in regular manner.

With reference to FIG. 13a, it should be observed that the adapter 3 can be made as a single part made of two different materials, e.g. by dual-injection or by being overmolded, with one of the materials being a substantially-rigid first material for forming the bottom portion 33, and the other being a deformable second material for forming the top portion 34. In the embodiment in FIG. 13a, the top portion 34 forms a peripheral bead that is flattened by the bushing 35 so as to bear both against the housing 11 and the probe 2.

In the embodiment in FIG. 13b, the adapter is molded in a single material. Its top portion 34 forms a peripheral groove in which the bushing is pressed in such a manner as to widen the groove and push its side walls respectively towards the housing and towards the probe.

The action of the bushing on the adapter thus generates at least local or partial deformation of the adapter that expands sideways.

Although the present invention is described above with reference to an imaging and treatment head incorporating both imaging means and treatment means, it can easily be understood that some characteristics, in particular the insulating trim 17, can be implemented on other types of treatment head that do not necessarily include imaging means. The various inventive characteristics make it possible to make a therapeutic head that is accurate, effective, and powerful. The adapter makes it possible to position the imaging means in removable but accurate manner, the position of the evacuation channel provides effective bubble removal, and the insulating trim makes it possible to increase the power of the treatment means considerably. Such a head makes it possible to treat tumors, concretions, bones, or more generally any organ of a living being.

The invention claimed is:

1. An imaging and treatment head for imaging and treating an organ or tissue of a living being, and usable in particular for treating tumors of the prostate or the thyroid, said head comprising:
    imaging means comprising an ultrasonic probe that are suitable for emitting waves or radiation so as to provide an imaged representation of an organ or tissue for treatment; and
    treatment means that are suitable for treating said organ or tissue locally, the treatment means being suitable for emitting waves or radiation so as to treat the organ or the tissue;
    said head being characterized in that the imaging means are mounted in removable manner on an adapter that ensures positioning of the imaging means relative to the treatment means, wherein the removable mounting of the imaging means does not require a disassembly of said head.

2. The head according to claim 1, further comprising a mounting body including a fastener zone for fastening the treatment means, and
a mounting housing for mounting the imaging means, said mounting housing receiving said adapter in which the imaging means are mounted in a removable manner.

3. The head according to claim 2, further comprising a propagation space containing a propagation medium that is suitable for transmitting the waves or radiation emitted by the imaging means and/or the treatment means, the mounting body forming a window that puts the housing in communication with the propagation space,
    said imaging means including a tip portion and a base portion, said tip portion incorporating an emitter face for emitting waves or radiation, and for being received in the adapter in such a manner as to emit through the window in the propagation space.

4. The head according to claim 3, wherein said adapter includes a front wall that is positioned in front of the emitter face of the imaging means and that closes the window at least in part, said front wall forming a diverging lens that is suitable for distancing the focal point (FP) of the waves or radiation emitted through the lens and the propagation space.

5. The head according to claim 2, wherein said adapter includes a sealing ring that ensures sealing between the imaging means and the mounting housing, the imaging means advantageously deforming the ring while they are being inserted into the ring.

6. The head according to claim 2, further comprising a compression bushing that deforms the adapter, at least in part, in its housing, so as to press it in a leak-tight manner against the imaging means.

7. The head according to claim 6, wherein the adapter includes a bottom portion that is substantially non-deformable and dimensionally stable, and a top portion that is deformable, the bottom portion ensuring accurate positioning of the imaging means, and the top portion ensuring sealing, the bottom and top portions advantageously being made of different materials.

8. The head according to claim 7, wherein the body forms an elongate window, the linear array being positioned so as to emit through the window, the treatment means being positioned on either side of the elongate window.

9. The head according to claim 2, wherein said imaging means is held in a position in said adapter by means of a holding system that is suitable for urging the imaging means into said adapter.

10. The head according to claim 2, wherein said imaging means comprises an ultrasonic probe having a linear array.

11. The head according to claim 2, wherein said treatment means comprises a focused piezoelectric transducer of the high intensity focused ultrasound ("HIFU") type.

* * * * *